(12) United States Patent
Yavitz et al.

(10) Patent No.: US 9,095,566 B1
(45) Date of Patent: Aug. 4, 2015

(54) EYELASH AND EYELID MARGIN INFECTIONS

(71) Applicants: Edward Quicksilver Yavitz, Loves Park, IL (US); Lory Posteraro, Loves Park, IL (US)

(72) Inventors: Edward Quicksilver Yavitz, Loves Park, IL (US); Lory Posteraro, Loves Park, IL (US)

( * ) Notice: Subject to any disclaimer, the term of this patent is extended or adjusted under 35 U.S.C. 154(b) by 0 days.

(21) Appl. No.: 14/133,780

(22) Filed: Dec. 19, 2013

Related U.S. Application Data

(60) Provisional application No. 61/840,637, filed on Jun. 28, 2013.

(51) Int. Cl.
*A61K 33/38* (2006.01)
*A61K 33/00* (2006.01)

(52) U.S. Cl.
CPC ..................... *A61K 33/38* (2013.01)

(58) Field of Classification Search
CPC ............... A61K 33/38; A61K 33/00
See application file for complete search history.

(56) References Cited

U.S. PATENT DOCUMENTS

| | | | |
|---|---|---|---|
| 3,697,643 A | 10/1972 | Shepherd et al. | |
| 4,423,031 A | 12/1983 | Murui et al. | |
| 4,677,143 A | 6/1987 | Laurin et al. | |
| 4,915,955 A | 4/1990 | Gomori | |
| 4,988,502 A | 1/1991 | Ounanian et al. | |
| 5,013,543 A | 5/1991 | Mercado et al. | |
| 5,053,221 A | 10/1991 | Robertson et al. | |
| 6,720,006 B2 | 4/2004 | Hanke et al. | |
| 7,087,249 B2* | 8/2006 | Burrell et al. | 424/618 |
| 7,470,437 B2* | 12/2008 | Burrell et al. | 424/618 |
| 7,700,131 B2 | 4/2010 | Taylor et al. | |
| 2009/0022765 A1 | 1/2009 | Chung et al. | |

FOREIGN PATENT DOCUMENTS

EP 2018839 12/2011

* cited by examiner

*Primary Examiner* — Blessing M Fubara
(74) *Attorney, Agent, or Firm* — Duane Morris LLP

(57) ABSTRACT

The present invention relates to compositions comprising silver nanoparticles for treating eyelash and eyelid margin infections and to methods of treating eyelash and eyelid margin infections, including infections by fungi, mites (e.g., *Demodex folliculorum*) and lice (e.g., *Pediculus humanus capitis*). We describe exemplary compositions, which may be formulated as a mascara for enhancing the appearance of the eyes, and their use in treatment of such infections.

21 Claims, No Drawings

EYELASH AND EYELID MARGIN INFECTIONS

This non-provisional application claims priority to U.S. Provisional Patent Application Ser. No. 61/840,637, filed Jun. 28, 2013, the entirety of which is incorporated by reference.

FIELD OF THE INVENTION

The present invention is generally related to methods of treating eyelash and eyelid margin infections and more particularly to methods of using a mascara composition comprising silver nanoparticles for treatment of eyelash and eyelid margin infections.

BACKGROUND OF THE INVENTION

A variety of single cellular and multicellular pathogens including bacteria, fungi, mites (e.g., *Demodex folliculorum*) and lice (e.g., *Pediculus humanus capitis*) can infect the eyelashes, the eyelid margin and the base of the eyelash follicles. The initial symptoms of eyelid margin infections can be mild, so that patients may not seek treatment until the infection has advanced to include symptoms such as burning, flaking, crusting, tearing, irritation, itching, redness in eyelid margins, a gritty, foreign body sensation and light sensitivity. Left untreated, eyelid margin infections can have serious consequences, including permanent scarring of the lid margins, loss of the eyelashes, and misdirected eyelashes, which in turn, can result in various sight-threatening corneal lesions. For example, misdirected eyelashes can induce trauma to the corneal epithelium leading to corneal ulceration and pannus formation, i.e., abnormal blood vessel or fibrous tissue growth in the cornea. Moreover, parasitic infections due to mites (e.g., *Demodex folliculorum*) and lice (e.g., *Pediculus humanus capitis*) are often overlooked in differential diagnosis of corneal disease, resulting in further delays in treatment.

Present methods of treatment of eyelash and eyelid margin infections generally involve daily eyelid scrubbing with mild shampoo, or other cleansing formulas, application of warm compresses, and administration of topical or systemic antibiotics, or topical steroids. The efficacy any one of these methods varies depending on the particular pathogen. Eyelid scrubbing and antibiotics are typically ineffective against eukaryotic pathogens such as *Demodex*, lice or yeast. Remedies such as eyelid scrubbing require long-term patient compliance. Topical ointments may cause visual blurring, which may be difficult for some patients to tolerate. There is a continuing need for effective, broad spectrum and easy to use treatments for eyelash and eyelid margin infections.

SUMMARY OF THE INVENTION

Provided herein are methods for treating a subject having an infection of the eyelash or eyelid margin, the method comprising applying to the eyelash a therapeutically effective amount of a composition comprising about 1 part per million (ppm) to about 20 parts per million (ppm) of silver nanoparticles. The infection can be a parasitic, bacterial, viral, fungal or protozoal infection. The parasite can be a mite, e.g., *Demodex folliculorum, Demodex brevis* or a louse, e.g., *Pthirus pubis*, or *Pediculus humanus corporis*. The bacteria can be *Streptococcus pneumoniae, Staphylococcus aureus, Pseudomonas aeruginosa, Moraxella* spp., *Escherichia coli, Serratia marcescens, Propionobacterium acnes, Staphylococcus epidermidis, Corynebacterium* spp. In some embodiments, the composition comprises a mascara. The composition can be formulated as an emulsion, foam, gel, liquid, lotion, ointment, salve, paste or powder and applied with a brush, applicator, sponge or gauze. The method can include the step of identifying a subject in need of treatment.

The composition can include a wax, a humectant, an oil, a surface active agent emulsifier, a thickener, an alcohol, and optionally, a pigment. The wax can be beeswax, stearic acid, carnauba wax, and paraffin wax or a combination there of. The humectant can include propylene glycol; 1,2,6 hexanetriol; butylene glycol; dipropylene glycol; hexylene glycol; glycerin; triethylene glycol; phytantriol hexanediol; phytantriol hexanetriol; hyaluronic acid; inositol; glycogen; sorbitol; polyglyceryl sorbitol; glucose; fructose; xylitol; elastin; collagen; keratin; isoceteth-x; isolaureth-x; laneth-x; laureth-x; steareth-x; polyethylene glycol; and silicone copolyols. The pigment can be a mineral pigment or an organic pigment. The oil can be an organic, silicone, or hydrocarbon oil. The surface active agent emulsifier can be lecithin or glycerol monostearate. The thickener can be a polyorganosiloxane-containing polymer, a non-silicone polyamide copolymer, a hydrocarbon resin, and a styrene-containing copolymer. In some embodiments, the composition comprises from about 10% to about 20% by weight of lipid comprising at least one wax; from about 1% to about 4% by weight of a humectant; from about 10% to about 15% by weight of pigment; from about 2% to about 5% by weight of surface active agent emulsifier; from about 0.5% to about 3% by weight of thickener; from about 5% to about 10% by weight ethanol; and from about 40% to about 50% by weight of water.

The composition can be applied one or more times a day for at least about two to at least about 30 days. The composition can be applied to the distal end of the eyelash. The composition can be applied until a symptom of the infection in the subject improves. Exemplary symptoms of infection include blepharitis, itchiness of the eyes, lid margin inflammation, eyelash collarettes, cylindrical dandruff, foreign body sensation, meibomian gland dysfunction, marginal corneal vascularization, hordeolums, eyelash misdirection, eyelash loss, blepharoconjuntivitis, blepharokeratitis, or ocular rosacea. The method also include administering to the subject an antibiotic agent, an anti-parasitic agent, an anti-inflammatory agent, an analgesic agent or a cleansing agent or applying one or more cosmetic compositions to the eyelash or eyelid margins.

Also provided are methods of enhancing the appearance of the eyes in a subject, the method including applying to the eyelashes a composition comprising mascara, wherein the macsara comprises about 1 part per million (ppm) to about 20 parts per million (ppm) of silver nanoparticles, about 10% to about 20% by weight of lipid comprising at least one wax; from about 1% to about 4% by weight of a humectant; from about 10% to about 15% by weight of pigment; from about 2% to about 5% by weight of surface active agent emulsifier; from about 0.5% to about 3% by weight of thickener; from about 5% to about 10% by weight ethanol; and from about 40% to about 50% by weight of water.

Also provided are kits which can include for example, a measured amount of a mascara composition comprising about 1 part per million (ppm) to about 20 parts per million (ppm) of silver nanoparticles and one or more items selected from the group consisting of an applicator, packaging material, a package insert comprising instructions for use, and a sterile container.

DETAILED DESCRIPTION

The present invention is based, in part, on the inventor's discovery that compositions comprising silver nanoparticles applied to the eyelashes effectively treated bacterial and parasitic infections of the both eyelash and eyelid margin. More specifically, application of the compositions to the eyelashes, for example, the distal portion of the eyelash cilia, eliminated infections in areas of the eyelid margin, such as the lash follicles, sebaceous glands, including the sebaceous glands of Zeis, sweat glands, including the apocrine sweat glands of Moll, the eyelid mucosa and surrounding tissues, that were not in direct contact with the silver nanoparticle-containing compositions. Thus, application of the compositions to the eyelashes can provide an efficient way to deliver a therapeutically effective amount of silver nanoparticles to the tissues of the delicate eyelid margin, while at the same time, minimizing any potential side effects that might result from direct application.

Accordingly, the invention features compositions and methods that can be used to treat bacterial and parasitic infections of the both eyelash and eyelid margin. The compositions include silver nanoparticles, which can be formulated for application to the eyelashes. Useful formulations include those that are retained on the eyelashes and are wear resistant. In some embodiments, the compositions can be formulated as a mascara. When formulated as a mascara, the compositions can include one or more pigments or other cosmetic agents for darkening, coloring or thickening the eyelashes to enhance the appearance of the eyes. The invention is not so limiting however, and the compositions can be formulated to be clear or transparent, i.e., to contain little or no colorants. Such compositions can be used as a basecoat and/or topcoat for application beneath and/or on to other products applied to eyelashes and are particularly suitable for those users who need treatment for eyelash and eyelid pathogens, but prefer not to color their lashes, for example men or children, or women who may not wish to color their lashes.

The methods of the invention include methods of administering the compositions to a patient to treat bacterial and parasitic infections of the eyelash and eyelid margin. The particular method of applying the compositions to the eyelashes can vary, depending in part on the nature of the formulation, e.g., a liquid, cake, cream, gel, or paste. In general, the compositions can be applied by using, for example, a brush, applicator, applicator wand, sponge, pad or gauze or by using the fingers or fingertips. The therapeutic methods described herein can be carried out in conjunction with other anti-infective therapies (e.g., an antimicrobial agent, an anti-parasitic agent, an anti-inflammatory agent, an analgesic agent or a cleansing agent) or with other cosmetic preparations. (e.g., a mascara or eyeliner).

Compositions

The compositions described herein include silver nanoparticles. Nanoparticles are typically between about 0.5 nm and about 100 nm in size. Atoms within a nanoparticle tend behave as a single unit with respect to their chemical and physical properties. Nanoparticles generally have properties that differ from those of the bulk material from which they are synthesized. Silver nanoparticles can be synthesized by any chemical, physical or biological method known in the art or can be purchased from commercial sources. A useful silver nanoparticle preparation is colloidal silver, i.e., silver nanoparticles homogeneously dispersed in a medium, for example, an aqueous solution. Colloidal silver nanoparticles (MesoSilver®) can be purchased Purest Colloids, Inc., Westhampton, N.J. Other sources include Utopia Silver and Natural Path Silver Wings.

The silver nanoparticles can vary in size from about 0.1 nM to about 100 nM (e.g. from about 0.1 nM, about 0.2 nM, about 0.3 nM, about 0.4 nM, about 0.5 nM, about 0.55 nM, about 0.6 nM, about 0.65 nM, about 0.70 nM, about 0.8 nM, about 0.9 nM, about 1.0 nM, about 2.0 nM, about 3.0 nM, about 5.0 nM, about 6.0 nM, about 7.0 nM, about 8.0 nM, about 9.0 nM, about 10.0 nM, about 15.0 nM, about 20.0 nM, about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM, about 100 nM, about 105 nM, about 110 nM.

The concentration of silver nanoparticles can vary. Useful colloidal silver formulations include those that contain about 99.9% pharmaceutical grade silver in an aqueous solution. Concentrations of colloidal silver can be expressed as parts per million (ppm). Typical colloidal silver formulations range from about 5 ppm to about 20 ppm. The compositions described herein can include silver nanoparticle concentrations of about 1 part per million (ppm) to about 10 parts per million (ppm) of silver nanoparticles; about 1 part per million (ppm) to about 7.5 parts per million (ppm) of silver nanoparticles; about 1 part per million (ppm) to about 5.0 parts per million (ppm) of silver nanoparticles; about 1 part per million (ppm) to about 3.0 parts per million (ppm) of silver nanoparticles; about 1 part per million (ppm) to about 2.5 parts per million (ppm) of silver nanoparticles; or about 1 part per million (ppm) to about 2.0 parts per million (ppm) of silver nanoparticles.

Colloidal silver solutions can also be characterized based on the relative particle surface area per milliliter of colloidal solution. Useful colloidal silver solutions can have a particle surface area ranging from about 0.1 $cm^2$/ml to about 200 $cm^2$/ml, about 10 $cm^2$/ml to about 120 $cm^2$/ml, or about 104.7 $cm^2$/ml.

Alternatively, the concentration of silver nanoparticles can be expressed as a percentage of a particular colloidal silver solution. For example, compositions of the invention can range from about 2% to about 20% of a colloidal silver solution, from about 2% to about 20%, about 2% to about 4%, about 3% to about 5%, about 4% to about 6%, about 4% to about 10%, about 6% to about 8%, about 6% to about 10% of a colloidal nanoparticle silver solution that has a particle surface area of about 104.7 $cm^2$/ml and a nanoparticle concentration of about 20 ppm.

The nanoparticle colloidal metal contained in the compositions includes silver and any of its alloys, oxides, thiols, humates, carbides, nitrides, borides, sulfides, halides and hydrides. Other metal-containing materials with biocidal properties, e.g., gold, platinum, copper, palladium, zinc, antimony, or bismuth are also contemplated.

The compositions of the invention also include one or more of a variety of other ingredients that function to provide pigmentation and/or lengthen and thicken the lashes when the compositions are formulated as a mascara; promote adherence of the compositions to the eyelashes; confer water resistance, e.g., resistance to moisture from human secretions such as tears, sebum, sweat and moisture from exposure to rain, snow, swimming pools, or bathing; confer resistance to rubbing, smearing or other pressure; facilitate application; and preserve the compositions. Thus the compositions can include or exclude pigments, thickeners, waxes, oils, surface active agents, humectants, alcohol and water. In some embodiments, the compositions can include at least one lipid selected from oils, waxes, fats, and combinations thereof; a humectant; a water-soluble fatty acid ester or soap; one or more film forming resins; a metallic or other color pigment; a surface active agent; a thickener; low molecular weight alcohol having from 1 to 7 carbon atoms, and water.

In some embodiments, the composition is formulated as a mascara, a cosmetic product used to enhance the eyes by darkening, thickening, lengthening or curling the eyelashes. Mascara formulations can vary, but these generally include one or more pigments or thickening agents. The pigment can include or exclude white, colored, inorganic, organic, polymeric, nonpolymeric, coated and uncoated pigments. Mineral pigments can include or exclude, for example, titanium dioxide, optionally surface-treated, zirconium oxide, zinc oxide, cerium oxide, iron oxides, chromium oxides, manganese violet, ultramarine blue, chromium hydrate, and ferric blue. Organic pigments generally consist of insoluble metallic salts of certified color additives, referred to as the Lakes. Organic pigments can include or exclude, for example, carbon black, pigments of D & C type, and lakes based on cochineal carmine, barium, strontium, calcium, and aluminum, azo, indigoid, triphenylmethane, anthroquinone, and xanthine dyes which are designated as D&C and FD&C blues, browns, greens, oranges, reds, and yellows.

The pigment concentration can vary depending on the specific pigment and the desired cosmetic effect. In some embodiments, the pigment concentration can range from to about 50% by weight of the composition, for example, from about 0.5% to about 40%, about 2% to about 30%, about 4% to about 50%, about 5% to about 20%, about 10% to about 40%, about 15% to about 30%, about 20% to about 50%, about 25% to about 30%, about 10% to about 15%. Exemplary pigment ranges include between 10% and 15% by weight of iron oxides.

When formulated as a mascara, the compositions can include one or more thickeners to enhance eyelash fullness. The thickener can include or exclude polyorganosiloxane-containing polymers, non-silicone polyamide copolymers, hydrocarbon resins, styrene-containing copolymers, or mixtures thereof. Other thickeners known in the art can be used. Such thickeners can include or exclude dextrin fatty acid ester, bentonite, xanthan gum, cellulose gum. polyacrylates with hydrophobic side groups, cellulose ethers with hydrophobic side groups, polyurethane thickeners and hydroxypropylethylcellulose. The thickener is generally from about 0.5% to about 3% by weight of one or more of the thickeners recited above.

Regardless of whether the composition is formulated as a mascara, i.e., with the addition of pigments and/or thickeners to enhance the appearance of the eyes, the compositions can include a wax, i.e., an organic compound comprising one or more long alkyl chains. Waxes can be malleable or solid and rigid at room temperature. Waxes can be derived from animal, plant, mineral, petroleum, or synthetic sources or can be a mixture of waxes from different sources, e.g., a wax derived from an animal, e.g., beeswax, plus a wax, derived from petroleum, e.g, paraffin wax. Waxes can also be obtained by catalytic hydrogenation of animal or plant oils comprising linear or branched $C_8$-$C_{32}$ fatty chains. Waxes can include or exclude, for example, beeswax, lanolin wax; rice wax, Japan wax, carnauba wax, candelilla wax, stearic acid, microcrystalline waxes, paraffins, petroleum jelly, ozokerite, polyethylene waxes, the waxes obtained by Fisher-Tropsch synthesis and waxy copolymers, and esters thereof, The wax concentration can vary, but useful amounts range from about 3% to about 20% by weight, e.g., about 3%, about 4%, about 5%, about 6%, about 7%, about 8%, about 9%, about 10%, about 11%, about 12%, about 13%, about 14%, about 15%, about 16%, about 17%, about 18%, about 19%, about 20%. Exemplary formulations can include about 12% beeswax and about 4% stearic acid or about 11')/0 paraffin.

The compositions can include one or more oils. In some embodiments, the compositions are formulated as an emulsion. Suitable emulsion forms include but are not limited to oil-in-water, water-in-oil, oil-in-water-in-oil, water-in-oil-in-water, multiple emulsion (W/O/W or O/W/O) and nanoemulsions (emulsions whose oil globules are of very fine particle size, that is to say that they have a number-average size of less than about 100 nanometers (nm)). Emulsions contain at least one oil phase and at least one aqueous phase. Useful oils are those that are pourable at room temperature (25° C.). Such oils may be volatile or nonvolatile; or organic, silicone, or hydrocarbon oils. Useful oils can include or exclude, for example, branched silicones such as methyl trimethicone; linear volatile silicones such as hexamethyldisiloxane, octamethyltrisiloxane, decamethyltetrasiloxane, dodecamethylpentasiloxane; cyclic volatile silicones generically referred to as "cyclomethicone", e.g., cyclotetrasiloxane, cyclopentasiloane, or cyclohexasiloxane; volatile hydrocarbons, e.g, $C_{9-12}$ paraffinic hydrocarbons such as isododecane, isohexadecane; nonvolatile silicones such as dimethicone, phenyl trimethicone, phenyldimethicone, diphenyldimethicone, trimethylsiloxyphenyldimethicone, cetyl dimethicone; nonvolatile organic oils e.g., naturally occurring plant oils such as soybean, castor seed, wheat germ, grape seed, almond, lavender; synthetic or naturally occurring mono-, di-, or triesters including esters of $C_{6-30}$ fatty carboxylic acids and mono-, di-, or polyhydric alcohols having from about 2 to 40 carbon atoms, e.g., isostearyl malate, diisostearyl malate, isononyl isononanoate, myristyl myristate, diglyceryl diisostearate, glyceryl stearate, glyceryl isostearate, polyglyceryl-3 isostearate, polyglyceryl-3 diisostearate; isopropyl esters, stearyl esters, capriolic esters, oleic acid esters, polymer oils and mineral oils.

When formulated as an emulsion, the compositions can also include one or more surfactants or surfactant-like materials that stabilize to the emulsions and inhibit de-phasing of the emulsions. Exemplary surface active agents include lecithin and glycerol monostearate. Useful concentration of surface active agent emulsifiers are from about 2% to about 5% by weight. Alternatively or in addition, the compositions can include or exclude one or more of a nonionic surfactant, e.g., alkoxylated alcohols, or ethers, carboxylic acids, silicone surfactants, anionic surfactants, cationic, zwitterionic and betaine surfactants.

The compositions can include a humectant, i.e., an agent that promotes moisture retention. Humectants cam include or exclude, for example, propylene glycol, 1,2,6 hexanetriol, butylene glycol, dipropylene glycol, hexylene glycol, glycerin, triethylene glycol, phytantriol, hexanediol, hexanetriol, hyaluronic acid, inositol, glycogen, sorbitol, polyglyceryl sorbitol, glucose, fructose, xylitol, elastin, collagen, keratin, isoceteth-x, isolaureth-x, laneth-x, laureth-x, steareth-x, PEG-x (polyethylene glycol) silicone copolyols, glucose, fructose, honey, hydrogenated honey, inositol, maltose, mannitol, maltitol, sorbitol, sucrose, xylitol, and xylose. The humectant can be about 1% to about 4% by weight of the composition, e.g., about 1%, about 1.5%, about 2%, about 2.5%, about 3%, about 3.5%, or about 4%.

When formulated as a mascara, the compositions of the invention can include one or more additives known in the art. Thus, for example, the compositions can include or exclude film forming agents; dispersants; antioxidants; essential oils; hydrocarbon-based oils; silicone oils; preserving agents; emulsifiers; sequestering agents; fragrances; natural or synthetic fibers, e.g., nylon, silk, polyethylene, polyethylene terephthalate, polypropylene, or microdenier fibers; silicone gels; dimethylaminoethyl methacrylate; water-insoluble polymeric materials; liposoluble polymers that are dispersible in the medium; fillers; shape memory polymers (SMP), wherein said SMP is a co-polymerized acrylic acid and stearyl acrylate polymer cross-linked with methylenebisacrylamide and sodium acrylate; neutralizing agents; cross-linkable siloxane polymers; synthetic prostaglandin agonists; cosmetic and hydrophilic and lipophilic active principles; proteins; antioxidants; fragrances; surfactants; fatty acid esters; emulsifiers; pigmenting agents; depigmenting agents; keratolytic agents; sequestering agents; polymers; pH adjusting agents; dermatological active agents such as, for example, emollients, moisturizers, vitamins, essential fatty acids; one fatty alkoxylated dimeric compounds; and mixtures thereof.

When formulated as a mascara, the compositions of the invention can include one or more powders known in the art. Useful powders include colored or non-colored (for example white) non-pigmented powders. They may be present in amounts ranging from about 0.01 to 40% by weight of the composition. Thus, for example, the compositions can include or exclude bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

In some embodiments, the compositions can include one or more alcohols, for example, ethanol or polyvinyl alcohol. Useful concentrations of ethanol can be from about 1% to about 20%, e.g., about 2%, about 3%, about 4%, about 5%, about 6%, about 7%, about 8%, about 9%, about 10%, about 11%, about 12%, about 15%, about 18%, about 20%.

Regardless of their original source or the manner in which they are obtained, the compositions of the invention can be formulated in accordance with their use using any standard art-known method. Pharmaceutical compositions and formulations for topical administration may include emulsions, ointments, lotions, creams, foams, gels, sprays, liquids, pastes, salves, or powders. Conventional pharmaceutical carriers, aqueous, powder or oily bases, thickeners may be used. The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well-known reference text in this field, and in the USP/NF (United States Pharmacopeia and the National Formulary).

A useful formulation method involves preparation of an emulsion. The details of the steps can vary depending on the specific ingredients and their relative concentrations, but typically the hydrophobic ingredients, e.g., the waxes, oils, and emulsifier are combined and heated. Separately, the water and other water soluble ingredients, e.g., ethanol, polyvinyl alcohol, thickeners (if present) are combined and heated. The two mixtures are then combined in a homogenizer or other apparatus and homogenized to form an emulsion. Pigments, if used, can be added to the oil mixture, the water mixture or both, or to the emulsion formed after homogenization. The silver nanoparticles are added during the homogenization step or mixed into the emulsion once it is formed. Alternatively, the compositions can be formulated by mixing the waxes, oils, pigments (if used), heating and agitation. In this method, the silver nanoparticles can be added along with the other ingredients or they can be added once the other ingredients have been combined.

Methods of Treatment

The compositions disclosed herein are generally and variously useful for treatment of infections of the eyelashes and eyelid margins. A patient is effectively treated whenever a clinically beneficial result ensues. This may mean, for example, a complete resolution of the symptoms of an infection, a decrease in the severity of the symptoms of the infection, or a slowing of the infection's progression. These methods can further include the steps of a) identifying a subject (e.g., a patient and, more specifically, a human patient) who has an infection of the eyelashes and/or eyelid margins; and b) providing to the subject a silver nanoparticle composition described herein. An amount of such a composition provided to the subject that results in a complete resolution of the symptoms of an infection, a decrease in the severity of the symptoms of the an infection, or a slowing of the an infection's progression is considered a therapeutically effective amount. The present methods may also include a monitoring step to help optimize dosing and scheduling as well as predict outcome. In some methods of the present invention, one can first identify the particular microorganism, e.g., a particular species of parasite or bacteria that has infected the patient. Monitoring can also be used to detect the onset of tolerance, to rapidly distinguish responsive patients from nonresponsive patients or to assess recurrence an infection. Where there are signs of tolerance or nonresponsiveness, a clinician can choose an alternative or adjunctive agent before the infection worsens.

Infections amenable to the therapeutic methods of the invention can be those involving an infectious agent susceptible to the cytotoxic effects of silver nanoparticles and silver ions. Silver and other metals are described as "oligodynamic," that is, they are effective anti-microbials even at extremely low concentrations. The biocidal mechanism of action of silver and other noble metals is not completely understood, but appears to involve multiple pathways including, for example, an increase in free radical production, an increase in membrane permeability, a disruption of iron homeostasis, and disruption of enzymes involved in disulfide bond formation. While we believe we understand certain events that occur in the course of treatment, the compositions of the present invention are not limited to those that work by affecting any particular cellular mechanism. Any infection involving an infectious agent susceptible to the cytotoxic effects of silver nanoparticles and silver ions is within the scope of the invention.

An infectious agent can be a parasite. Exemplary parasites include mites, e.g., *Demodex folliculorum, Demodex brevis*, and lice, e.g., *Pthirus pubis, Pediculus humanus corporis*. *Demodex* mites are the most common microscopic ectoparasite found in the human skin. The rate of *Demodex* infestation increases with age. *Demodex* is found at a higher density in patients with rosacea and has been implicated as a causative agent in other skin diseases such as *pityriasis folliculorum*, perioral dermatitis scabies-like eruptions, facial pigmentation, eruptions of the bald scalp, demodicosis gravis, and basal cell carcinoma. Because the eye is surrounded by such protruding body parts as the nose, the brow, and the cheek, the eyelid is not as accessible as the face to daily cleansing hygiene. Once *Demodex* infestation is established on the face, it can spread to the eyelids. The entire life cycle of *Demodex*

*folliculorum* takes places in the time span of 18-24 days. During the day, they feed on dead skin cells within hair follicles. At night, they emerge onto the surface to mate and lay eggs in hair follicles. A female adult lays 20-24 eggs in a single hair follicle. As they grow, the eggs become tightly packed, and develop into larvae. The larva are then washed by a sebaceous flow, produced by the host's sebaceous glands, into the mouth of the hair follicle where they mature into adults.

*Demodex* can damage the eyelid margins in several ways. *Demodex folliculorum*, feeds on epithelial cells at the hair follicle resulting in follicular distention and the formation of loose or misdirected lashes. Micro-abrasions caused by the mite's claws can induce epithelial hyperplasia and reactive hyperkeratinization around the eyelash base, forming cylindrical dandruff. *D. brevis* can mechanically block the orifices of meibomian glands, causing meibomian gland dysfunction with lipid tear deficiency. *D. brevis* burrows into the meibomian glands where its chitinous exoskeleton may act as a foreign body causing granulomatous reaction. Thus, *Demodex* mites may be a potential cause of recurrent and refractory chalazia. *Demodex* mites also act as vectors for bacteria by carrying *Streptococci* and Staphylococci on their surfaces and *Bacillus oleronius* internally.

*Pediculus humanus capitis* or head lice and the closely related pubic or crab louse (*Pthirus pubis*) are hematophagic ectoparasites, that is, wingless insects spending their entire life on human hair and eyelashes, feeding exclusively on human blood at the base of the follicles. Symptoms of lice infections include itchiness of the eyelid margin, fatigue, red, scaly, and thickened eyelids, tearing, conjunctivitis and some loss of the eyelashes. Lice infections are more common in younger people.

An infectious agent can be a bacterium. Exemplary bacteria include *Streptococcus pneumoniae, Staphylococcus aureus, Pseudomonas aeruginosa, Moraxella* spp., *Escherichia coli, Serratia marcescens, Propionobacterium acnes Staphylococcus epidermidis, Corynebacterium* spp. An infectious agent can be a fungus. Exemplary fungi include *Pityrosporum ovale, Aspergillus* spp., *Alternaria* spp., *Aureobasidium* spp., *Candida albicans, Histoplasma* spp., *Cladosporium* spp., *Epicoccum* spp., *Fusarium* spp., *Helminthosporium* spp., *Phoma* spp., and *Rhizopus* spp. An infectious agent can be a virus. Exemplary viruses include herpesviruses and adnoviruses. An infectious agent can be a protozoa. Exemplary protozoa include *Leishmania, Acanthamoeba keratitis, Toxoplasma* spp., *Microsporidia* spp., *Trypanosoma* spp., and *Plasmodium* spp.

The compositions and methods described herein are also useful for the treatment of a subject infected with more than one species of infectious agent, for example, two or more different species of parasites; two or more different species of bacteria; two or more different species of viruses; or two or more different species of protozoa. The compositions and methods described herein are also useful for the treatment of a subject infected a combination of two or more kinds infectious agents, for example, a parasite and a bacteria; a parasite and a virus; a parasite and a protozoa; a bacteria and a virus, a bacteria and a protozoa; a virus and protozoa.

The methods disclosed herein can be applied to a wide range of species, e.g., humans, non-human primates (e.g., monkeys), horses or other livestock, other mammals kept as laboratory animals.

The methods of the invention can be expressed in terms of the preparation of a medicament. Accordingly, the invention encompasses the use of the agents and compositions described herein in the preparation of a medicament. The compounds described herein are useful in therapeutic compositions and regimens or for the manufacture of a medicament for use in treatment of diseases or conditions as described herein (e.g., an infection disclosed herein).

The compositions described herein can be applied to the eyelashes of a subject, i.e., a patient, in need of treatment. The compositions can be applied to the eyelashes using any art known method. For example, the compositions can be applied using a brush, applicator wand, comb, sponge, or gauze. The compositions can be applied along all or substantially all of the length of the eyelashes. Alternatively, the compositions can be applied to the distal end of the eyelashes. In some embodiments, the compositions can be instilled directly upon the surface of the eye as an ocular biocidal. Formulations for direct instillation can comprise silver nanoparticles, boric acid, carboxymethylcellulose, and glycerin in an aqueous solution. An exemplary formulation, which can be administered as a eyedrop four times daily, includes 30% Mesosilver®; 3% boric acid, 0.5% carboxymethylcellulose, and 1.5% glycerin.

The dosage required will depend on the nature of the formulation, the nature of the patient's infection, the patient's size, weight, surface area, age, and sex, other drugs being administered, and the judgment of the attending clinicians. Suitable dosages are in the range of about 0.5 ppm to about 100 ppm of silver nanoparticles. Wide variations in the needed dosage are to be expected in view of the variety of infectious agents and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Useful dosage regimens can include application every 2, 4, 6, 8, 10, 12, 14, 16, 18, 24, 36, or 48 hours.

The duration of treatment with any composition provided herein can be any length of time from as short as one day to as long as several weeks or several months. For example, a composition can be administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or for 1, 2, 3, 4, 5, 6 weeks or more. It is also noted that the frequency of treatment can be variable. For example, the present compounds can be administered once (or twice, three times, etc.) daily, weekly, or monthly. In addition, treatments can be repeated following periods when no treatment is given.

An effective amount of any composition provided herein can be administered to a patient in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician. In some embodiments, the patient can be monitored for a reduction in symptoms of infection for example, blepharitis (e.g. anterior blepharitis, which is characterized by inflammation of the anterior lid margin, or posterior blepharitis which is characterized by reduced tear quality and dry eyes or mixed anterior and posterior blepharitis) itchiness of the eyes, lid margin inflammation, eyelash collarettes, cylindrical dandruff, foreign body sensation, dry eyes, meibomian gland dysfunction, marginal corneal vascularization, hordeolums, eyelash misdirection, eyelash loss, blepharoconjuntivitis, blepharokeratitis, trichiasis, madarosis, punctate corneal erosions, corneal ulceration, chalazia, or ocular rosacea.

The presence of the infectious agent can also be monitored directly. For example, levels of *Demodex* can be monitored by microscopic examination of an eyelash sample and directly counting the number of parasites. Alternatively, levels of infections agents can be monitored by other laboratory methods including polymerase chain reaction (PCR), immunoassays, or standard laboratory culture methods.

The compositions may also be administered with another therapeutic agent, such as an antibiotic agent (e.g., tetracycline; erythromycin; topical azothromicin; cyclosporin A; tobramycin/dexamethasone, levoflaxacin, ciloxan, moxifloxacin 0.5%/dexamethasone, tea tree oil); an anti-parasitic agent (e.g., mercury oxide 1% ointment, pilocarpine gel, sulfur ointment, camphorated oil, tea tree oil) an anti-inflammatory agent (e.g., a topical corticosteroid), an analgesic agent, a cleansing agent (e.g. mild or "baby" shampoo) or a nutritional supplement (e.g. omega-3 supplementation). Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Articles of Manufacture

The compositions described herein can be packaged in suitable containers labeled, for example, for use as a therapy to treat an infection of the eyelash or eyelid margin The containers can include the compound and one or more of a suitable stabilizer, carrier molecule, and/or the like, as appropriate for the intended use. Accordingly, packaged products (e.g., sterile containers containing one or more of the compositions described herein and packaged for storage, shipment, or sale at concentrated or ready-to-use concentrations) and kits, including at least one composition of the invention, e.g., a composition comprising about 1 part per million (ppm) to about 100 parts per million (ppm) of silver nanoparticles and instructions for use, are also within the scope of the invention. A product can include a container (e.g., a vial, jar, bottle, bag, or the like) containing one or more compositions of the invention. In addition, an article of manufacture further may include, for example, packaging materials, one or more applicators, e.g., a brush, applicator wand, comb, sponge, or gauze and instructions for use.

In some embodiments, the kits can include one or more additional therapeutic agents, for example, an antibiotic agent (e.g., tetracycline), an anti-parasitic agent, an anti-inflammatory agent, an analgesic agent or a cleansing agent. The additional agents can be packaged together in the same container as the compostions of the invention or they can be packaged separately. The product may also include a legend (e.g., a printed label or insert or other medium describing the product's use (e.g., an audio- or videotape)). The legend can be associated with the container (e.g., affixed to the container) and can describe the manner in which the compositions therein should be administered (e.g., the frequency and route of administration), indications therefor, and other uses. The compositions can be ready for administration (e.g., present in dose-appropriate units), and may include one or more additional pharmaceutically acceptable adjuvants, carriers or other diluents and/or an additional therapeutic agent. Alternatively, the compositions can be provided in a concentrated form with a diluent and instructions for dilution.

EXAMPLES

Example 1

An oil in water (o/w) emulsion mascara having the following composition was prepared as discussed below. The ingredients in the formulation are shown in Table 1.

TABLE 1

Oil-in-Water Mascara Formulation (Mascara Formulation I)

| Ingredient | Amount (% by Weight) |
|---|---|
| beeswax | 12 |
| strearic acid | 4 |
| glycerol monostearate | 2.5 |
| iron oxide | 10 |
| dimethylaminoethyl methacrylate (DM) | 4 |
| triethanolamine | 2 |
| polyquaternium-11 | 1.5 |
| colloidal silver | 10 |
| ethanol | 10 |
| deionized water | 44 |

The beeswax, stearic acid, and glyceryl monostearate were combined and heated to 80° C. Triethanolamine surfactant and DM were dispersed or dissolved in the deionized water and ethanol. This water mixture was also heated to 80° C., then gradually added to the oil mixture, with stirring, and uniformly emulsified. The black iron oxide pigment and colloidal silver (MesoSilver®, Purest Colloids, Inc.) were added to and uniformly dispersed in the emulsion. The pH was adjusted to between 7.2-7.8 and the mascara was allowed to cool.

A 52 year old patient with bilateral *staphylococcus* blepharitis applied the mascara formulation above to her right eye daily for two weeks and an identical mascara minus the colloidal silver to her left eye. The mascara of the present invention incorporating colloidal silver reduced the signs of eyelid blepharitis, including redness and eyelash collarettes, on the right eye compared to the left eye by slit lamp examination, representing a reduction in the bacteria count.

Example 2

The mascara formulation of Example 1 was applied daily to the eyelashes of both eyes of a patient with *Pediculus* lice and eggs observed on the eyelashes. The live lice were manually removed at a slit lamp with fine forceps prior to the first application of the invented mascara. No further lice were observed over a period of one month, demonstrating the ability of the invented mascara to kill lice eggs and any subsequent hatched live lice.

Example 3

A mascara composition containing colloidal silver solution (MesoSilver®, Purest Colloids, Inc.) for application to the eyelashes was prepared as follows. The ingredients are shown in Table 2.

TABLE 2

Mascara Formulation II

| Ingredient | Amount (% by Weight) |
| --- | --- |
| propylene glycol | 2 |
| glyceryl monostearate | 5 |
| paraffin wax | 11 |
| polyvinyl alcohol | 4 |
| ethanol | 4 |
| deionized water | 50 |
| magnesium silicate triethanolamine | 3 |
| colloidal silver solution (MesoSilver, Purest Colloids, Inc.) | 6 |
| iron oxides (black) | 15 |

The ingredients of the oil phase (propylene glycol; glyceryl monostearate; and paraffin wax) were heated to 80-85° C., while mixing until uniformly mixed. The ingredients of the aqueous phase (deionized water; polyvinyl alcohol; and ethanol) were heated to 80-85° C., while mixing until uniformly mixed. The aqueous phase was added to the oil phase with homogenization mixing for 5 minutes, then the silicate, pigment and silver were added and homogenized another 5 minutes. The mixture was then allowed to cool to room temperature. The mascara formulation was applied with a curved brush applicator daily to the eyelashes of a 40 year old woman with chronic hordeolums (bacterial infections of the eyelid sebaceous glands). A hordeolum which was present at the start of treatment resolved and no further hordeolums were observed for a period of 6 months.

What is claimed is:

1. A method for treating a subject having a parasitic infection of the eyelash, wherein the parasite is a mite or a louse, the method comprising applying to the eyelash a therapeutically effective amount of a composition comprising about 1 part per million (ppm) to about 20 parts per million (ppm) of silver nanoparticles.

2. The method of claim 1, wherein the mite is *Demodex folliculorum, Demodex brevis*, and the louse is *Pthirus pubis*, or *Pediculus humanus corporis*.

3. The method of claim 1, wherein the composition comprises a mascara.

4. The method of claim 1, wherein the composition is applied with a brush or applicator.

5. The method of claim 1, further comprising the step of identifying a subject in need of treatment.

6. The method of claim 1, wherein the composition comprises about 1 part per million (ppm) to about 10 parts per million (ppm) of silver nanoparticles; about 1 part per million (ppm) to about 7.5 parts per million (ppm) of silver nanoparticles; about 1 part per million (ppm) to about 5.0 parts per million (ppm) of silver nanoparticles; about 1 part per million (ppm) to about 3.0 parts per million (ppm) of silver nanoparticles; about 1 part per million (ppm) to about 2.5 parts per million (ppm) of silver nanoparticles; or about 1 part per million (ppm) to about 2.0 parts per million (ppm) of silver nanoparticles.

7. The method of claim 1, wherein the composition comprises about 1.25 parts per million (ppm) of silver nanoparticles or about 2.0 parts per million (ppm) or silver nanoparticles.

8. The method of claim 1, wherein the silver nanoparticles have a particle size of about 0.5 nM to about 100 nM.

9. The method of claim 1, wherein the composition comprises from about 2% to about 20% of a colloidal silver solution, wherein the colloidal silver solution has a particle surface area of about 0.1 $cm^2$/ml to about 200 $cm^2$/ml.

10. The method of claim 1, wherein the composition comprised from about 6% to about 10% of a solution of colloidal silver, wherein the colloidal silver solution has a particle surface area of about 10 $cm^2$/ml to about 120 $cm^2$/ml.

11. The method of claim 1, wherein the composition comprised from about 6% to about 10% of a solution of colloidal silver, wherein the colloidal silver solution has a particle surface area of about 104.7 $cm^2$/ml.

12. The method of claim 1, wherein the composition further comprises a wax, and optionally, a pigment.

13. The method of claim 1, wherein the composition is applied one or more times a day.

14. The method of claim 13, wherein the administration occurs for at least about two to at least about 30 days.

15. The method of claim 14 wherein the administration occurs for at least about two days; at least about 4 days; at least about 7 days; at least about 10 days; at least about 14 days; at least about 18 days; at least about 21 days; at least about 25 days; at least about 28 days; or at least about 30 days.

16. The method of claim 1 wherein the composition is applied to the distal end of the eyelash.

17. The method of claim 1, where in the composition is applied until a symptom of the infection in the subject improves.

18. The method of claim 17, where a symptom of infection includes eyelid margin inflammation.

19. The method of claim 1, further comprising administering to the subject an anti-inflammatory agent.

20. The method of claim 1, further comprising applying one or more cosmetic compositions to the eyelash or eyelid margins.

21. A method of enhancing the appearance of the eyes in a subject having a parasitic infection of the eyelash, wherein the parasite is a mite or a louse, the method comprising applying to the eyelashes a composition comprising mascara; wherein the mascara comprises about 1 part per million (ppm) to about 20 parts per million (ppm) of silver nanoparticles, about 10% to about 20% by weight of lipid comprising at least one wax; from about 1% to about 4% by weight of a humectant; from about 10% to about 15% by weight of pigment; from about 2% to about 5% by weight of surface active agent emulsifier; from about 0.5% to about 3% by weight of thickener; from about 5% to about 10% by weight ethanol; and from about 40% to about 50% by weight of water.

* * * * *